United States Patent
Okada et al.

(10) Patent No.: US 7,851,206 B2
(45) Date of Patent: Dec. 14, 2010

(54) NUCLEIC ACID DETECTION DEVICE

(75) Inventors: Jun Okada, Tokyo (JP); Sadato Hongo, Yokohama (JP); Nobuhiro Gemma, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 952 days.

(21) Appl. No.: 11/682,484

(22) Filed: Mar. 6, 2007

(65) Prior Publication Data

US 2007/0227885 A1 Oct. 4, 2007

(30) Foreign Application Priority Data

Mar. 29, 2006 (JP) ............................... 2006-092030

(51) Int. Cl.
*C12M 1/34* (2006.01)
*C12M 3/00* (2006.01)
(52) U.S. Cl. ............................... 435/287.2; 204/403.01; 435/6; 435/283.1; 435/287.1; 435/288.3
(58) Field of Classification Search ..................... 435/6, 435/283.1, 287.1, 287.2, 288.3–288.7; 204/403.01
See application file for complete search history.

(56) References Cited

U.S. PATENT DOCUMENTS

| | | | |
|---|---|---|---|
| 5,776,672 A | 7/1998 | Hashimoto et al. | |
| 5,972,692 A | 10/1999 | Hashimoto et al. | |
| 6,294,670 B1 | 9/2001 | Takenaka | |
| 6,767,706 B2 * | 7/2004 | Quake et al. | ................ 435/6 |
| 6,787,368 B1 * | 9/2004 | Wong et al. | ................ 436/518 |
| 6,942,771 B1 * | 9/2005 | Kayyem | ................ 204/409 |
| 7,745,203 B2 * | 6/2010 | Hongo et al. | ............ 435/283.1 |
| 2002/0160427 A1 * | 10/2002 | Beier et al. | ................ 435/7.9 |
| 2005/0048561 A1 * | 3/2005 | Fulwyler et al. | ................ 435/6 |
| 2005/0158787 A1 | 7/2005 | Hongo et al. | |

FOREIGN PATENT DOCUMENTS

JP 5-199898 8/1993

(Continued)

OTHER PUBLICATIONS

U.S. Appl. No. 11/980,409, filed Oct. 31, 2007, Hongo, et al.

(Continued)

*Primary Examiner*—Walter D Griffin
*Assistant Examiner*—Shanta G Doe
(74) *Attorney, Agent, or Firm*—Oblon, Spivak, McClelland, Maier & Neustadt, L.L.P.

(57) ABSTRACT

A nucleic acid detection device includes a flow channel through which a solution containing a nucleic acid recognition body flows, probe electrodes having immobilized nucleic acid probes, and a counter electrode used to measure an electrochemical response of the nucleic acid recognition body. The flow channel includes a curved portion and a straight portion continued from and located downstream of the curved portion. The probe electrodes are arranged at intervals along the straight portion, avoiding an upstream end of the straight portion that is located within a distance L from the curved portion. The distance L is given by $L=0.065 \times Re \times D$, $Re=\rho u D/\mu$, and $D=4S/Lp$ where $\rho$, $u$, and $\mu$ are a concentration, a flow velocity, and a viscosity of the solution, and S and Lp are a sectional area and a wall peripheral perimeter of the flow channel, respectively.

25 Claims, 10 Drawing Sheets

FOREIGN PATENT DOCUMENTS

| | | |
|---|---|---|
| JP | 2000-50876 | 2/2000 |
| JP | 2004-61427 | 2/2004 |
| JP | 2004-125777 | 4/2004 |
| JP | 2004-309462 | 11/2004 |
| WO | WO 2004/061418 A2 | 7/2004 |
| WO | WO 2004/106546 A1 | 12/2004 |

OTHER PUBLICATIONS

Eric Nebling, et al., "Electrical Detection of Viral DNA Using Ultramicroelectrode Arrays", Analytical Chemistry, vol. 76, No. 3, Feb. 1, 2004, pp. 689-696.

U.S. Appl. No. 12/483,840, filed Jun. 12, 2009, Okada, et al.

U.S. Appl. No. 11/848,623, filed Aug. 31, 2007, Hongo, et al.

* cited by examiner

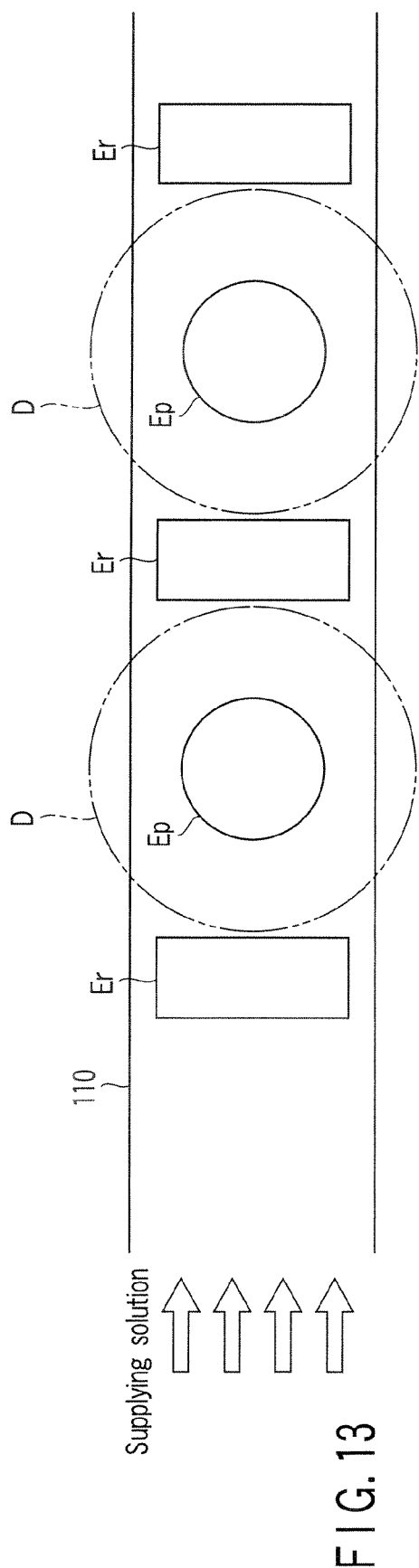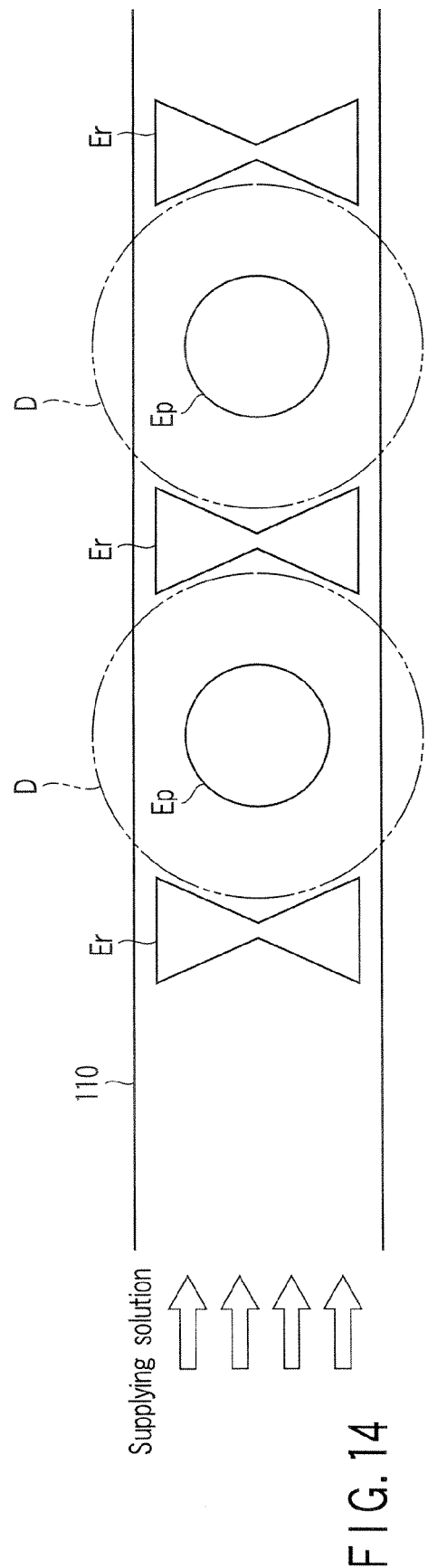

NUCLEIC ACID DETECTION DEVICE

CROSS-REFERENCE TO RELATED APPLICATIONS

This application is based upon and claims the benefit of priority from prior Japanese Patent Application No. 2006-092030, filed Mar. 29, 2006, the entire contents of which are incorporated herein by reference.

BACKGROUND OF THE INVENTION

1. Field of the Invention

The present invention relates to a nucleic acid detection device used to a target nucleic acid detection utilizing the electrochemical response of a nucleic acid recognition body.

2. Description of the Related Art

As genetic engineering develops in recent years, disease diagnosis or prevention using a gene has become possible in the medical field. This is called gene diagnosis. Detecting a human gene defect or change that causes a disease allows the disease to be diagnosed or predicted precritically or at its very early stage. Along with human genome decoding, researches on the relationship between the genotype and disease advance. Treatments that match the genotype of the individual patients (tailor-made medical care) are being put into practice. Accordingly, it is very important to detect a gene and determine a genotype simply.

Examples of nucleic acid detection methods include a method using a radioisotope and a method using a fluorescent dye label. The former method can perform detection only at limited locations and requires cumbersome operation. The latter method requires an expensive apparatus to detect a fluorescent dye.

Besides these techniques, another technique has been established. According to this technique, a sample nucleic acid is hybridized with a nucleic acid probe immobilized to the surface of an electrode. Then, a nucleic acid recognition body is added and electrochemically detected. The technique of electrochemically detecting a nucleic acid is suitable to "Lab-on-a-chip" of causing reactions on a single chip. Hence, this technique has been under development in a variety of applications.

Various types of nucleic acid recognition bodies are available. Various types of nucleic acid recognition bodies are exists. For example double stranded nucleic acid recognition body which recognizes the double stranded nucleic acid. Assume that the electromechanical response of the nucleic acid recognition body is to be measured to detect the presence/absence of a target nucleic acid. In this case, whether the recognition body is adsorbed by a double stranded nucleic acid, a single stranded nucleic acid, or an electrode surface cannot be discriminated. Hence, in addition to the electrochemical response caused by hybridization of the target nucleic acid, a background electrochemical response (reference value, negative control) caused by adsorption to the single stranded nucleic acid or the electrode surface exists. This is regarded as the defect of the scheme that detects a nucleic acid by using the electrochemical response of the nucleic acid target body in comparison with the scheme that detects a nucleic acid with a fluorescent dye. If the nucleic acid recognition body concentration is high, the background electrochemical response (reference value) increases. If the nucleic acid recognition body concentration is low, the electrochemical response caused by hybridization decreases. Hence, the nucleic acid recognition body concentration must be so set as to fall within an optimal concentration range.

The nucleic acid hybridization is easily influenced by the temperature, salt concentration, the pH of the solution, the flow velocity of the solution, and the like. The nucleic acid recognition body should be reacted in such a condition that a nucleic acid bond in which the target nucleic acid hybridizes with the nucleic acid probe will not be dissociated.

According to one nucleic acid detection device that supplies a nucleic acid recognition body by utilizing a flow channel, in order to increase the length of the flow channel, curved portions are formed midway along the flow channel so the flow channel meanders. In this nucleic acid detection device, the curve portions that exist midway along the flow channel disorder the flow of solution. The disordered flow of solution decreases the detection accuracy.

BRIEF SUMMARY OF THE INVENTION

A nucleic acid detection device according to the present invention comprises a flow channel that allows a solution containing a nucleic acid recognition body to flow through it, probe electrodes having immobilized nucleic acid probes, and a counter electrode used to measure an electrochemical response of the nucleic acid recognition body. The flow channel includes a curved portion and a straight portion that is continued from and located downstream of the curved portion. The counter electrode is provided in the flow channel. The probe electrodes are arranged at intervals along the straight portion so as to avoid an upstream end of the straight portion that is located within a distance L from the curved portion. The distance L is given by $L=0.065 \times Re \times D$, $Re = \rho u D / \mu$, and $D = 4S/Lp$ where $\rho$ is the concentration of the solution, $u$ is the flow velocity of the solution, $\mu$ is the viscosity of the solution, $S$ is the sectional area of the flow channel, and $Lp$ is the wall peripheral perimeter of the flow channel.

BRIEF DESCRIPTION OF THE SEVERAL VIEWS OF THE DRAWING

FIG. 13 shows probe electrodes and auxiliary electrodes in the conventional nucleic acid detection device;

FIG. 14 shows probe electrodes and auxiliary electrodes in a nucleic acid detection device according to the fifth embodiment.

DETAILED DESCRIPTION OF THE INVENTION

The embodiments of the present invention will be described with reference to the accompanying drawings.

Figure 1:
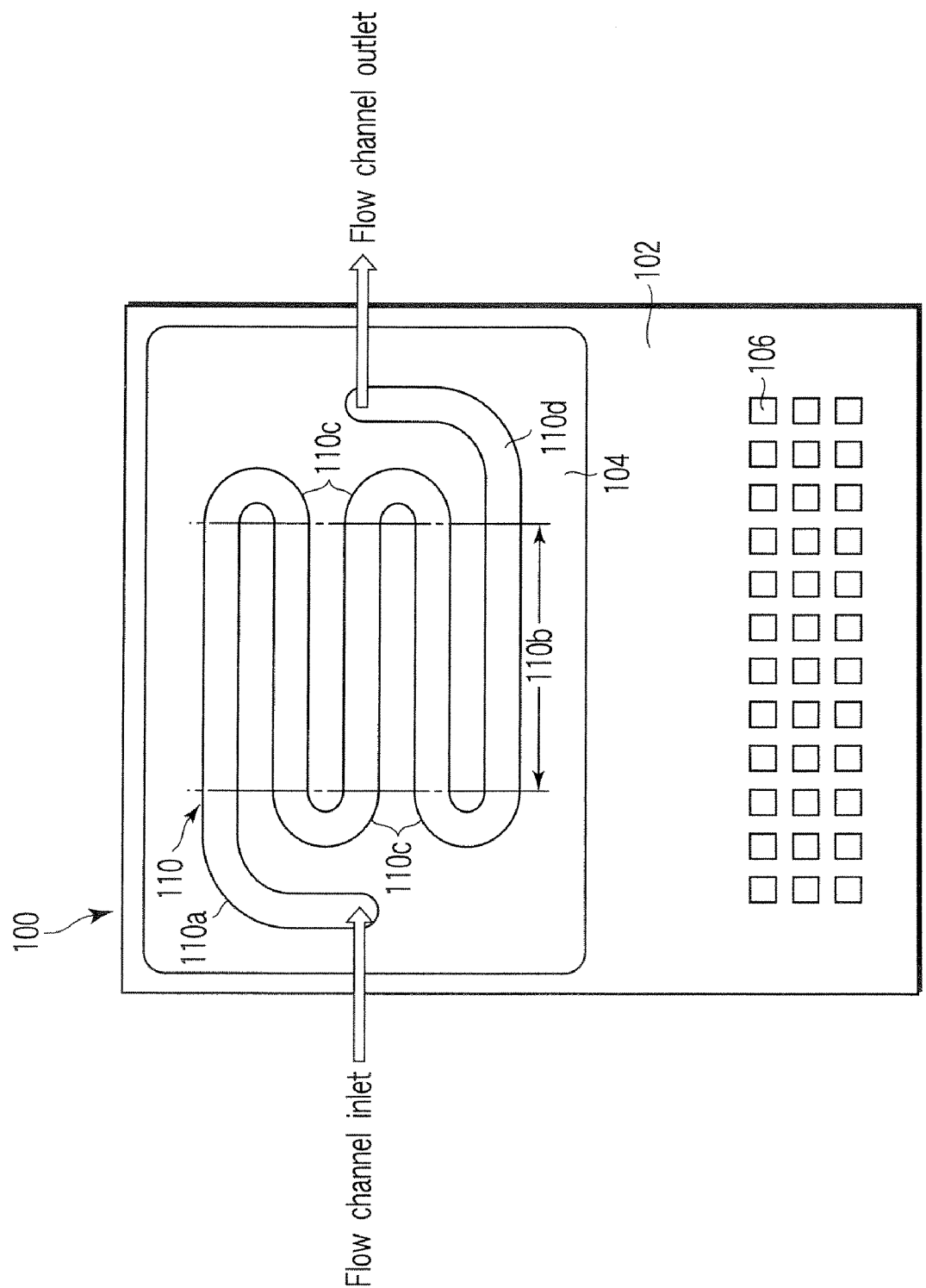
FIG. 1 shows a nucleic acid detection device to detect a nucleic acid electrochemically.

As shown in FIG. 1, a nucleic acid detection device 100 has a support substrate 102 and a flow channel regulation member 104. The support substrate 102 has signal input/output pads 106. The flow channel regulation member 104 has a flow channel 110 that allows a solution containing nucleic acid recognition bodies to flow through it.

The flow channel 110 has a flow channel inlet 110a located at the upstream end, a flow channel outlet 110d located at the downstream end, straight portions 110b, and semicircular curved portions 110c connecting the straight portions 110b. The straight portions 110b and the curved portions 110c are located between the flow channel inlet 110a and the flow channel outlet 110d. The straight portions 110b are arrayed parallel to each other. The curved portions 110c, which connect the straight portions 110b, need not be semicircular but can have, e.g., a curved shape or a bent shape of a straight line.

Although not shown, the nucleic acid detection device 100 has electrodes in the flow channel 110. The electrodes are arranged at intervals to form a row along the flow channel 110. The electrodes include probe electrodes to which nucleic acid probes are immobilized, and at least one auxiliary electrode to be used for measurement of the electrochemical response. The auxiliary electrode includes at least a counter electrode, and preferably both a counter electrode and a reference electrode. The electrodes are respectively electrically connected to the signal input/output pads 106 through wirings formed in or on the nucleic acid detection device 100.

The nucleic acid detection device 100 is used as it is mounted on a known nucleic acid detection apparatus. The nucleic acid detection apparatus supplies a solution containing nucleic acid recognition bodies to the flow channel 110 and measures the current flowing through the electrodes through the signal input/output pads 106.

The nucleic acid detection device 100 is not limited to the form shown in FIG. 1.

The nucleic acid detection device 100 may be formed by forming a groove in the flow channel regulation member 104, by stacking a flat member on the flow channel regulation member 104, by forming a groove in a flat member and stacking the flat member on the flow channel regulation member 104, or by forming grooves in both a flat member and the flow channel regulation member 104 and stacking the flat member on the flow channel regulation member 104. The flow channel 110 may be directly formed in the support substrate 102 to omit the flow channel regulation member 104. The sectional structure of the flow channel 110 may have an arbitrary shape, e.g., a polygon such as a square or a triangle, a semicircle, a semi-ellipse, or the like.

For example, according to a practical example, the width of the flow channel of the straight portion 110b and that of the curved portion 110c can fall within a range of 0.05 mm to 3.0 mm (both inclusive) and preferably 0.2 mm to 1.5 mm (both inclusive). The height of the flow channel of the straight portion 110b and that of the curved portion 110c can fall within a range of 0.02 mm to 2.0 mm (both inclusive) and desirably 0.1 mm to 1.2 mm (both inclusive). If the flow channel size falls within these ranges, variations in concentration of nucleic acid recognition bodies in the flow channel are suppressed.

The width of the flow channel 110 is always constant, but may vary to change from wide to narrow, narrow to wide, and wide to narrow repeatedly.

The signal input/output pads 106 on the support substrate 102 may be omitted when necessary. The nucleic acid detection device 100 may include a region to perform various types of reaction steps and other detections such as a nucleic acid extraction reaction, a nucleic acid amplification reaction, a filtration step, and a stirring step.

CONVENTIONAL EXAMPLE

Figure 2:
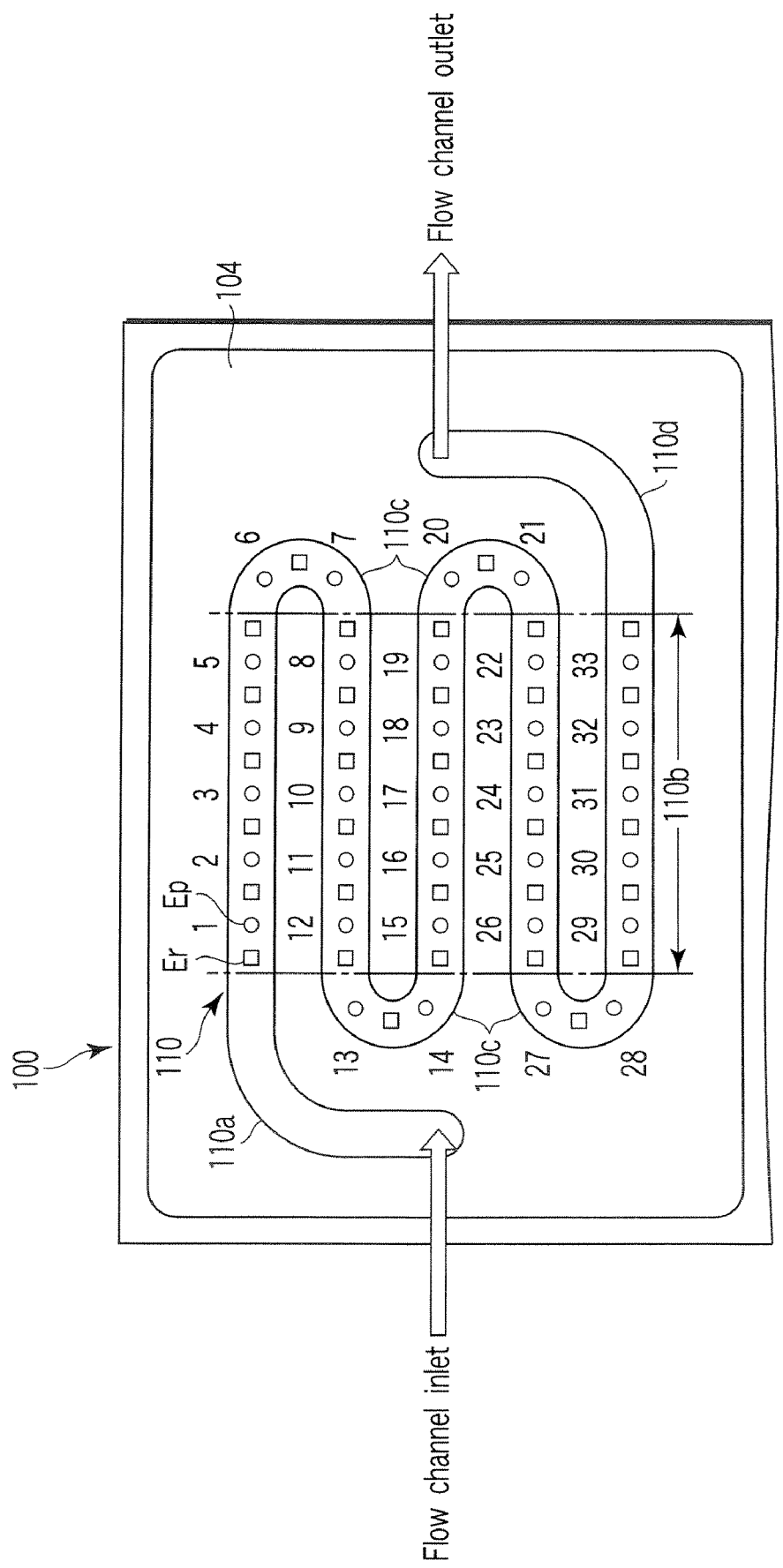
FIG. 2 shows the layout of electrodes in a conventional nucleic acid detection device.

As shown in FIG. 2, a conventional nucleic acid detection device 100 has probe electrodes Ep and auxiliary electrodes Er. The probe electrodes Ep are arranged at intervals along a flow channel 110 to form a row. The auxiliary electrodes Er are located among the probe electrodes Ep and at the two ends of the row of the probe electrodes Ep. The probe electrodes Ep and the auxiliary electrodes Er are located at both straight portions 110b and curved portions 110c.

Figure 3:
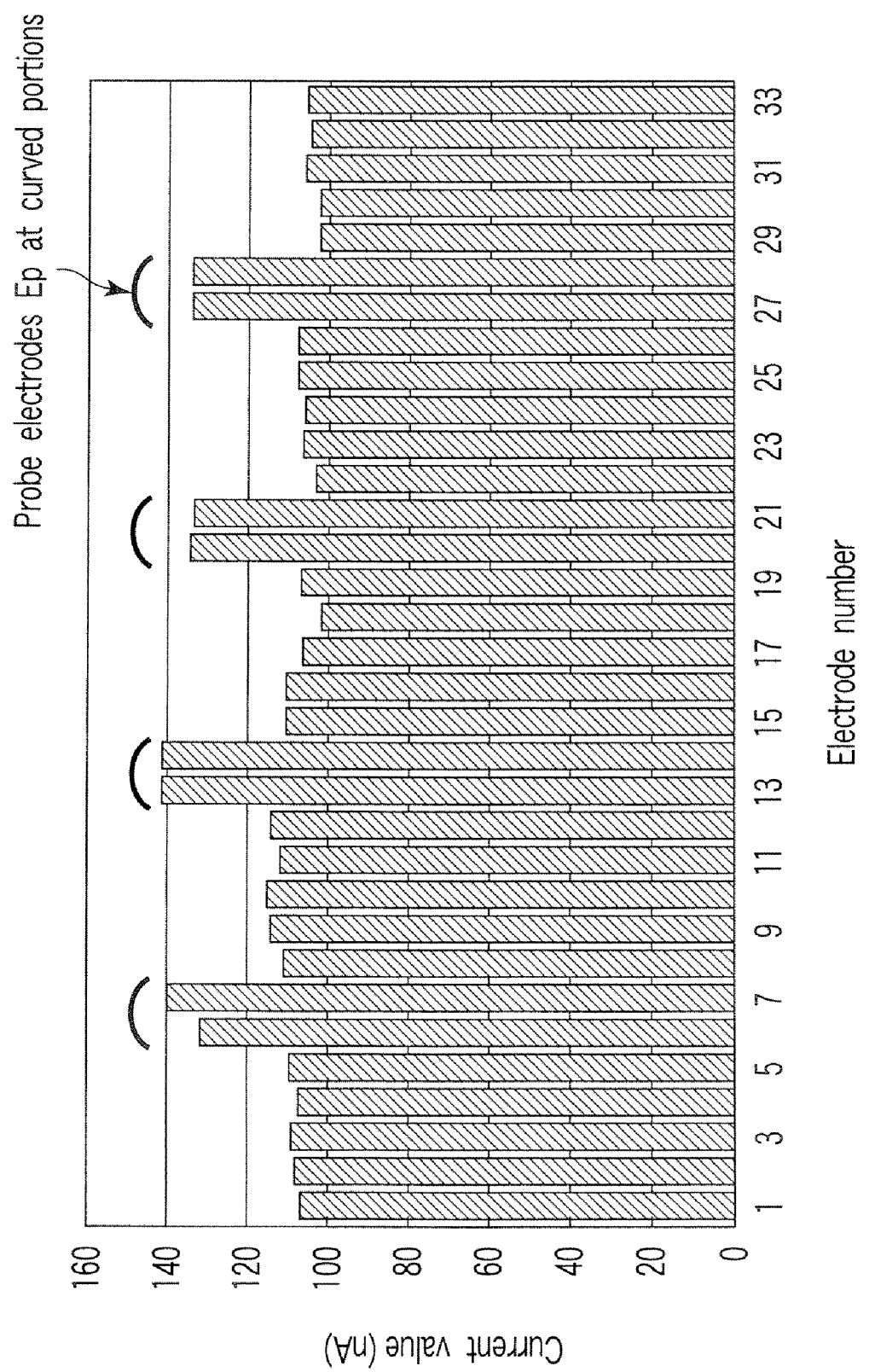
FIG. 3 shows the electrochemical response of a nucleic acid recognition body obtained in the nucleic acid detection device of FIG. 2.

In FIG. 3, the electrode numbers are assigned to the probe electrodes Ep in the order of 1, 2, 3, ... from the flow channel inlet side, as shown in FIG. 2. As is apparent from FIG. 3, with the probe electrodes Ep arranged at the curved portions 110c, larger current values are measured than with the other probe electrodes Ep arranged at the straight portions 110b. Namely, measurement results vary between the straight portions 110b and the curved portions 110c.

In the nucleic acid detection device, the flow of solution that has been stable at the straight portions 110b disorders when it enters the curved portions 110c. Namely, the flow conditions of solution changes between the straight portions 110b and the curved portions 110c. The flow of solution influences the hybridization of the nucleic acid, dissociation of the bond of the hybridized nucleic acid, the reaction of the nucleic acid recognition body, and the like. As a result, variations occur between the measurement results obtained by the probe electrodes Ep located at portions where the flow of solution disorders and the measurement results obtained by the probe electrodes Ep located at portions where the flow of solution is stable. These variations in measurement result decrease the detection accuracy.

First Embodiment

Figure 4:
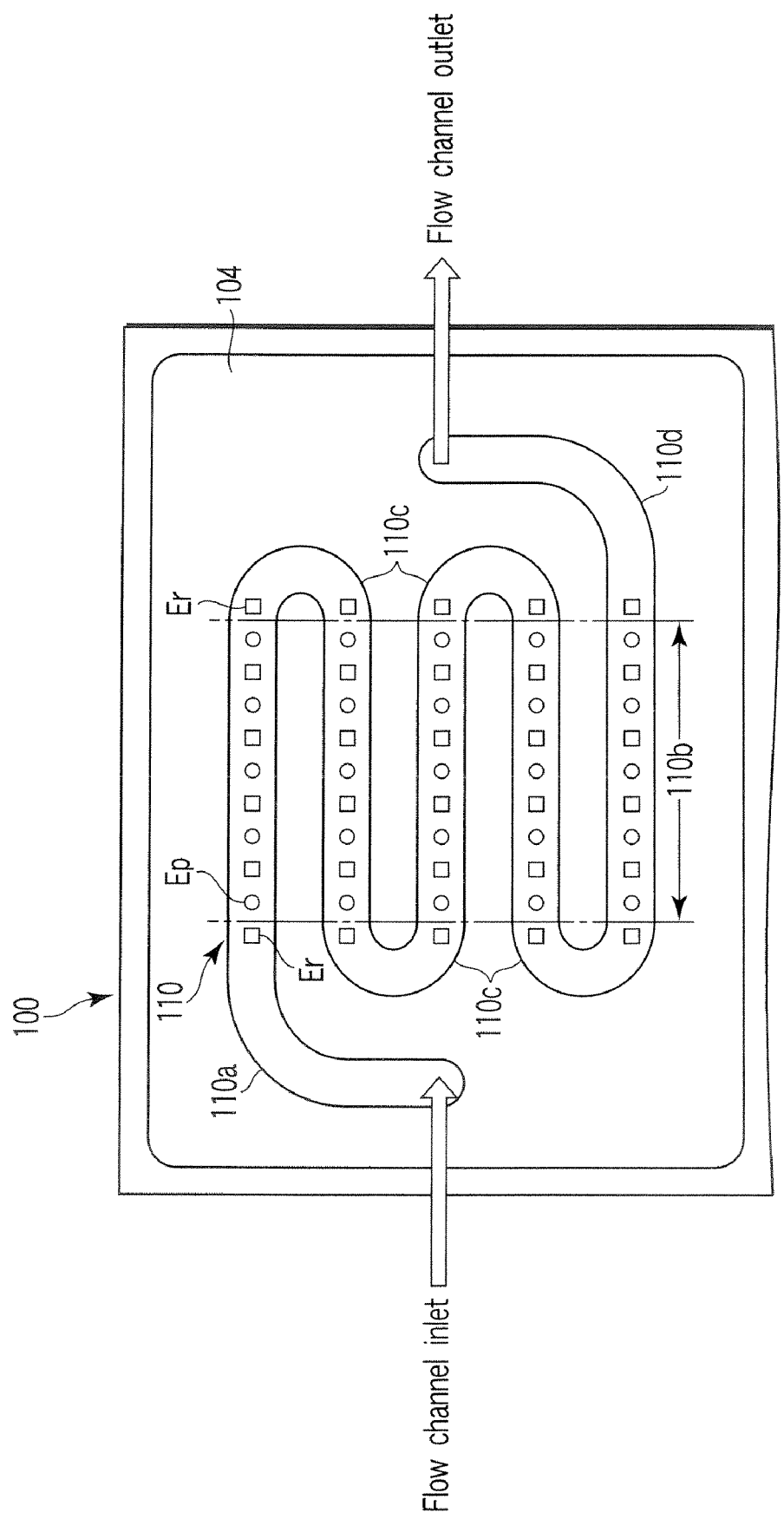
FIG. 4 shows the layout of electrodes in a nucleic acid detection device according to the first embodiment.

As shown in FIG. 4, a nucleic acid detection device 100 according to this embodiment has probe electrodes Ep and auxiliary electrodes Er. All the probe electrodes Ep are arranged at straight portions 110b. In other words, the probe electrodes Ep are arranged so as to avoid curved portions 110c. The auxiliary electrodes Er are arranged at the two ends of the row of the probe electrodes Ep located on each straight portion 110b and among the probe electrodes Ep.

Although the probe electrodes Ep and the auxiliary electrodes Er are arranged at regular intervals, they need not be arranged at regular intervals, but may be arranged at irregular intervals.

The auxiliary electrodes Er located at the two sides of each row of the probe electrodes Ep are located outside the corresponding straight portion 110b. Namely, the auxiliary electrodes Er at the two sides are located at the flow channel inlet 110a, the curved portions 110c, or the flow channel outlet 110d.

In this nucleic acid detection device, a probe electrode Ep is used for measurement together with an adjacent auxiliary electrode Er (the counter electrode or the counter and reference electrodes).

Figure 5:
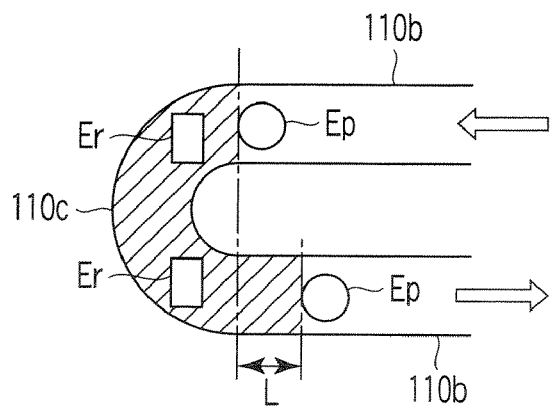
FIG. 5 shows a curved portion in the nucleic acid detection device of FIG. 4 in enlargement.
Figure 8:
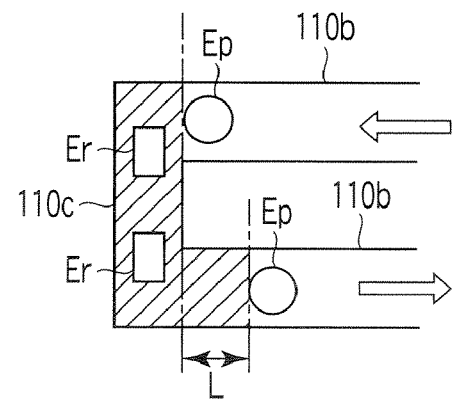
FIG. 8 shows still another curved portion that can replace the curved portion of FIG. 5.
Figure 6:
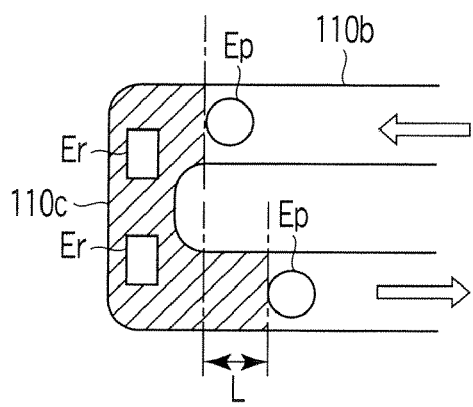
FIG. 6 shows another curved portion that can replace the curved portion of FIG. 5.
Figure 9:
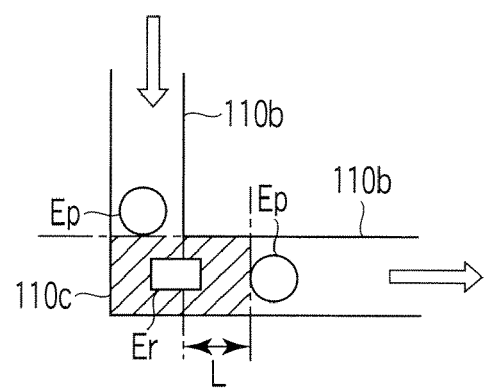
FIG. 9 shows still another curved portion that can replace the curved portion of FIG. 5.
Figure 7:
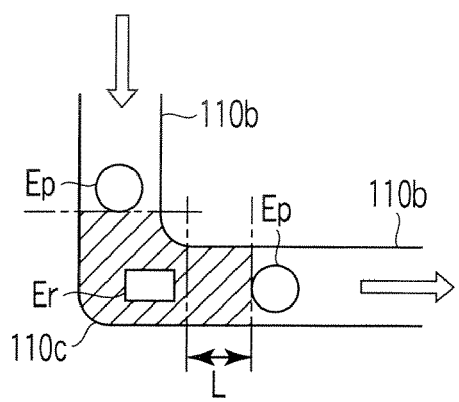
FIG. 7 shows still another curved portion that can replace the curved portion of FIG. 5.

Preferably, as shown in FIG. 5, the probe electrodes Ep are arranged so as to avoid the curved portions 110c and upstream ends of the straight portions 110b that are located within a distance L from the downstream end of the curved portion 110c. The distance L is given by the following equation:

$$L = 0.065 \times Re \times D$$

$$Re = \rho u D / \mu$$

$$D = 4S/Lp$$

where $\rho$ is the concentration of the solution, u is the flow velocity of the solution, $\mu$ is the viscosity of the solution, S is the sectional area of the flow channel, and Lp is the wall peripheral perimeter of the flow channel.

The distance L was determined on the basis of the following consideration.

When the solution flows in from the tube inlet at a uniform velocity, a boundary layer develops along the tube wall. When the boundary layer increases its thickness to reach the center, the velocity distribution in the tube becomes constant (e.g., a parabolic velocity distribution). The region until reaching the fully developed flow is called an entrance region, and its length is called an inlet length X.

In the case of a laminar flow, X/D is a function of Re. According to Boussinesq, $X/D \geq 0.065 \times Re$.

Whether an in-tube flow is a laminar flow or a turbulent flow is discriminated in accordance with the magnification of the dimensionless number Re that is defined by the following equation and named Reynolds number.

$$Re = \rho u l / \mu$$

where l is the typical length of the flow, u is the typical flow velocity, $\rho$ is the density of the fluid, and $\mu$ is the viscosity of the fluid. As the number Re is a dimensionless number, its value is the same regardless of the employed system of units as far as the state of the flow is the same. For a flow in the tube, $Re = \rho u D/\mu$ is employed by using an inner diameter D of the tube to substitute the typical length l of the flow.

When the section of the pipeline is not circular, if an equivalent diameter De defined by the following equation as the typical length of Re is employed, turbulent transition, pressure loss, and the like can be dealt with in the same manner as with a circular cylindrical tube.

$$De = 4S/lp$$

where S is the sectional area of the flow, and lp is the perimeter of the periphery of the solid wall with which the flow is in contact, i.e., a wetted perimeter.

In the above relations, when the inlet length X substitutes for the distance L and of the wetted perimeter lp substitutes for the wall peripheral perimeter Lp of the flow channel, the relationship described above is obtained.

With this consideration, if the auxiliary electrodes Er on the two sides of the row of the probe electrodes Ep are not located outside the corresponding straight portions 110b but on the straight portion 110b within the distance L from the downstream end of the corresponding curved portion 110c, the function does not change.

In the nucleic acid detection device of FIG. 4, semicircular curved portions are employed. However, the shapes of the curved portions are not limited to this, but can be as shown in FIGS. 6 to 9. Furthermore, the curved portions are not limited to the shapes shown in FIGS. 6 to 9, but can have any shapes. This discussion applies to a curved portion with any shape that connects straight portions.

As is apparent from the above description, according to this embodiment, all the probe electrodes Ep are arranged so as to avoid portions where the flow of solution disorders. In other words, the flow of solution at portions where the probe electrodes Ep are arranged is the same. Thus, variations in measurement result caused by a difference in flow of solution do not occur among the probe electrodes Ep. Namely, a decrease in detection accuracy caused by the disorder of the flow of solution due to the presence of the curved portions is avoided.

The nucleic acid detection device of this embodiment has the same number of probe electrodes Ep as in the conventional nucleic acid detection device. However, the horizontal length of a flow channel regulation member 104 decreases. Thus, the nucleic acid detection device 100 is downsized. This is apparent from comparison of FIGS. 2 and 4.

The nucleic acid detection device is preferably used as a disposable device, because it detects nucleic acids that are a fine, small-amount material. For this purpose, cost reduction of the nucleic acid detection device is sought for. Downsizing of the nucleic acid detection device 100 contributes to cost reduction. As the nucleic acid detection device 100 is downsized, the length of the flow channel decreases. A decrease in length of the flow channel contributes to a decrease in necessary sample amount.

Second Embodiment

Figure 10:
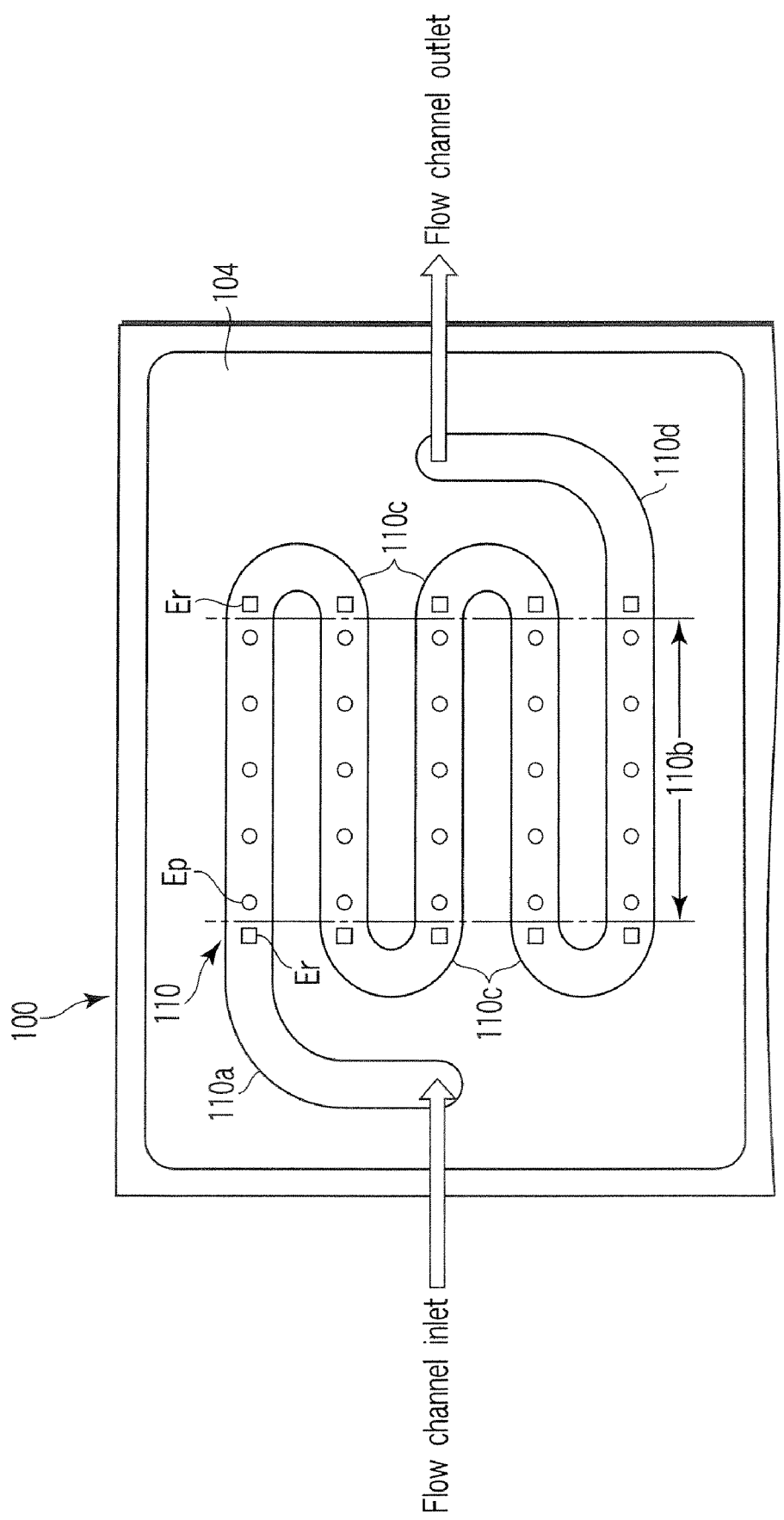
FIG. 10 shows the layout of electrodes in a nucleic acid detection device according to the second embodiment.

As shown in FIG. 10, a nucleic acid detection device 100 according to this embodiment has probe electrodes Ep and auxiliary electrodes Er, as in the first embodiment. All the probe electrodes Ep are arranged at straight portions 110b. The auxiliary electrodes Er are arranged at the two ends of the row of the probe electrodes Ep located on each straight portion 110b.

In this embodiment as well, preferably, the probe electrodes Ep are arranged so as to avoid the curved portions 110c and the upstream ends of the straight portions 110b that are located within a distance L from the downstream end of the curved portion 110c.

The auxiliary electrodes Er are located outside the straight portions 110b. More specifically, the auxiliary electrodes Er on the two sides are located at the flow channel inlet 110a, the curved portions 110c, or the flow channel outlet 110d. The auxiliary electrodes Er may be located at the portions of the straight portions 110b that are within the distance L from the downstream end of the corresponding curved portions 110c.

In this nucleic acid detection device, a probe electrode Ep is used for measurement together with the auxiliary electrodes Er (the counter electrodes or the counter and reference electrodes) that are located on the two sides of the straight portion 110b where the probe electrode Ep is located.

According to this embodiment, all the probe electrodes Ep are arranged so as to avoid portions where the flow of solution disorders, as in the first embodiment. Thus, a decrease in detection accuracy caused by the disorder of the flow of solution due to the presence of the curved portions is avoided.

The nucleic acid detection device of this embodiment has the same number of probe electrodes Ep as in the conventional nucleic acid detection device, as in the first embodiment. However, the horizontal length of a flow channel regulation member 104 decreases. Thus, the nucleic acid detection device 100 is downsized. Downsizing of the nucleic acid detection device 100 contributes to cost reduction. As the nucleic acid detection device 100 is downsized, the length of the flow channel decreases. A decrease in length of the flow channel contributes to a decrease in necessary sample amount.

In the nucleic acid detection device 100 of this embodiment, the same number of probe electrodes Ep as in the first embodiment are arranged at the straight portions 110*b*. Since no auxiliary electrodes Er are present among the probe electrodes Ep, a larger number of probe electrodes Ep may be arranged at shorter intervals. This increases the density of the probe electrodes Ep. This contributes to downsizing, i.e., cost reduction, of the nucleic acid detection device 100.

Third Embodiment

Figure 11:
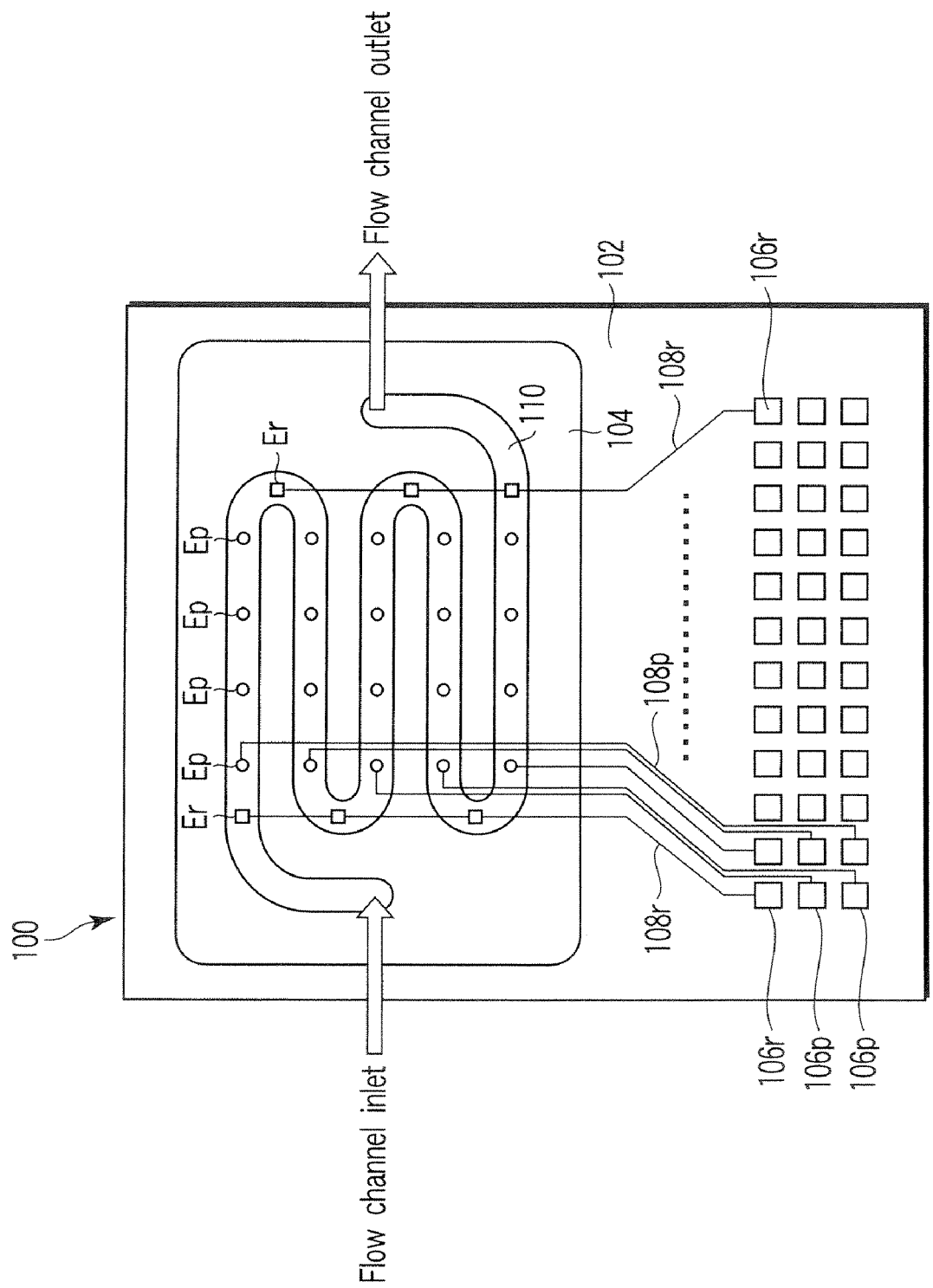
FIG. 11 shows the layout of electrodes and wirings in a nucleic acid detection device according to the third embodiment.

As shown in FIG. 11, a nucleic acid detection device 100 according to this embodiment has probe electrodes Ep and auxiliary electrodes Er, as in the first embodiment. All the probe electrodes Ep are arranged at straight portions 110*b*. More preferably, the probe electrodes Ep are arranged so as to avoid the curved portions 110*c* and the upstream ends of the straight portions 110*b* that are located within a distance L from the downstream end of the curved portion 110*c*.

The auxiliary electrodes Er are arranged so as to avoid the straight portions 110*b*. Hence, the auxiliary electrodes Er are located somewhere within the flow channel inlet 110*a*, the curved portions 110*c*, and the flow channel outlet 110*d*.

The auxiliary electrodes Er located on the left side are commonly connected to one auxiliary electrode pad 106*r* through one auxiliary electrode wiring 108*r*. Similarly, the auxiliary electrodes Er located on the right side are commonly connected to another auxiliary electrode pad 106*r* through one auxiliary electrode wiring 108*r*. Each probe electrode Ep is connected to one corresponding probe electrode pad 106*p* through one corresponding probe electrode wiring 108*p*.

In this nucleic acid detection device, a probe electrode Ep is used for measurement together with the auxiliary electrodes Er (the counter electrodes or the counter and reference electrodes) that are located near the straight portion 110*b* where the probe electrode Ep is located.

According to this embodiment, all the probe electrodes Ep are arranged so as to avoid portions where the flow of solution disorders, as in the first embodiment. Thus, a decrease in detection accuracy caused by the disorder of the flow of solution due to the presence of the curved portions is avoided.

The nucleic acid detection device of this embodiment has the same number of probe electrodes Ep as in the conventional nucleic acid detection device, as in the first embodiment. However, the horizontal length of a flow channel regulation member 104 decreases. Thus, the nucleic acid detection device 100 is downsized. Downsizing of the nucleic acid detection device 100 contributes to cost reduction. As the nucleic acid detection device 100 is downsized, the length of the flow channel decreases. A decrease in length of the flow channel contributes to a decrease in necessary sample amount.

In the nucleic acid detection device 100 of this embodiment, the same number of probe electrodes Ep as in the first embodiment are arranged at the straight portions 110*b*. Since no auxiliary electrodes Er are present among the probe electrodes Ep, a larger number of probe electrodes Ep may be arranged at shorter intervals. This increases the density of the probe electrodes Ep.

In the nucleic acid detection device 100 of this embodiment, the auxiliary electrodes Er are commonly connected to one auxiliary electrode pad 106*r* through one auxiliary electrode wiring 108*r*. The number of wirings is smaller than in an arrangement in which one auxiliary electrode pad 106*r* is connected to one auxiliary electrode Er, to simplify the layout of the wirings. This contributes to downsizing, i.e., cost reduction, of the nucleic acid detection device 100.

Fourth Embodiment

Figure 12:
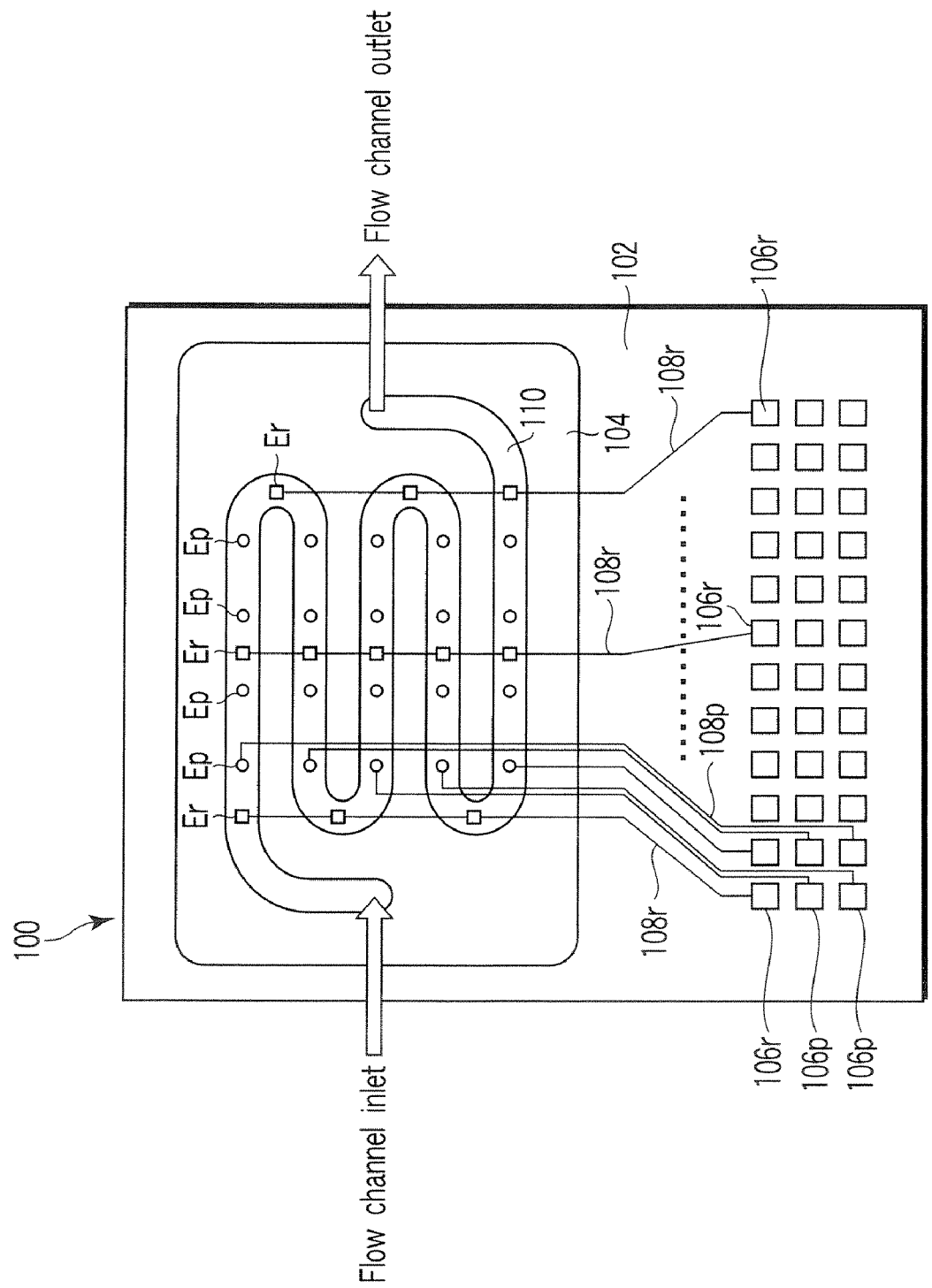
FIG. 12 shows the layout of electrodes and wirings in a nucleic acid detection device according to the fourth embodiment.

As shown in FIG. 12, a nucleic acid detection device 100 according to this embodiment has probe electrodes Ep and auxiliary electrodes Er, as in the first embodiment. All the probe electrodes Ep are arranged at straight portions 110*b*. More preferably, the probe electrodes Ep are arranged so as to avoid the curved portions 110*c* and the upstream ends of the straight portions 110*b* that are located within a distance L from the downstream end of the curved portion 110*c*.

The auxiliary electrodes Er are located at the centers of the straight portions 110*b*, the flow channel inlet 110*a*, the curved portions 110*c*, and the flow channel outlet 110*d*.

The auxiliary electrodes Er located on the left side are commonly connected to one auxiliary electrode pad 106*r* through one auxiliary electrode wiring 108*r*. Similarly, the auxiliary electrodes Er located on the right side are commonly connected to another auxiliary electrode pad 106*r* through one auxiliary electrode wiring 108*r*. The auxiliary electrodes Er located at the centers are commonly connected to still another auxiliary electrode pad 106*r* through one auxiliary electrode wiring 108*r*. Each probe electrode Ep is connected to one corresponding probe electrode pad 106*p* through one corresponding probe electrode wiring 108*p*.

In this nucleic acid detection device, a probe electrode Ep is used for measurement together with the auxiliary electrodes Er (the counter electrodes or the counter and reference electrodes) that are located before and after the probe electrode Ep along the flow channel 110.

According to this embodiment, all the probe electrodes Ep are arranged so as to avoid portions where the flow of solution disorders, as in the first embodiment. Thus, a decrease in detection accuracy caused by the disorder of the flow of solution due to the presence of the curved portions is avoided.

The nucleic acid detection device of this embodiment has the same number of probe electrodes Ep as in the conventional nucleic acid detection device, as in the first embodiment. However, the horizontal length of a flow channel regulation member 104 decreases. Thus, the nucleic acid detection device 100 is downsized. Downsizing of the nucleic acid detection device 100 contributes to cost reduction. As the nucleic acid detection device 100 is downsized, the length of the flow channel decreases. A decrease in length of the flow channel contributes to a decrease in necessary sample amount.

In the nucleic acid detection device 100 of this embodiment, the same number of probe electrodes Ep as in the first embodiment are arranged at the straight portions 110*b*. Alternatively, a larger number of probe electrodes Ep may be arranged at shorter intervals. This increases the density of the probe electrodes Ep.

In the nucleic acid detection device 100 of this embodiment, the auxiliary electrodes Er are commonly connected to one auxiliary electrode pad 106*r* through one auxiliary electrode wiring 108*r*. The number of wirings is smaller than in an arrangement in which one auxiliary electrode pad 106*r* is connected to one auxiliary electrode Er, to simplify the layout of the wirings. This contributes to downsizing, i.e., cost reduction, of the nucleic acid detection device 100.

Fifth Embodiment

The fifth embodiment is directed to a change in shape of the auxiliary electrodes Er in the nucleic acid detection device of the first embodiment shown in FIG. 4. That is, the arrangement of the nucleic acid detection device of the fifth embodiment is the same as that of the first embodiment except for the shape of the auxiliary electrodes Er.

Usually, the probe electrodes Ep, the auxiliary electrodes Er, the auxiliary electrode pads 106*r*, the probe electrode pads 106*p*, the probe electrode wirings 108*p*, and the auxiliary electrode wirings 108*r* are formed by patterning a metal thin film, and the patterned metal thin film is covered with a passivation film except for the centers of the probe electrodes Ep, the auxiliary electrodes Er, the auxiliary electrode pads 106*r*, and the probe electrode pads 106*p*. The effective sizes and shapes of these electrodes are defined by openings formed in the passivation film. Assume that the auxiliary electrodes comprise counter electrodes. As the counter electrodes are electrodes that receive the current from the probe electrodes, they preferably have sufficient sizes with respect to the probe electrodes.

The probe electrodes Ep are formed by dropping drops containing nucleic acid detection probes to portions exposed from the openings formed in the passivation film. The drops containing the nucleic acid detection probes must be dropped not to come into contact with the auxiliary electrodes Er. For this purpose, the probe electrodes Ep and the auxiliary electrodes Er are formed at gaps determined considering the sizes of the drops containing the nucleic acid detection probes. In general, the gap between the probe electrode Ep and the auxiliary electrode Er is set to fall within a range of, e.g., 0.1 mm to 3.0 mm (both inclusive) and preferably 0.5 mm to 2.5 mm (both inclusive).

As shown in FIG. 13, each ordinary auxiliary electrode Er (the counter electrode or the counter and reference electrodes) has a rectangular shape. The probe electrodes Ep and the auxiliary electrodes Er are arranged at such intervals that drops D dropped onto the probe electrodes Ep and containing the nucleic acid detection probes will not come into contact with the auxiliary electrodes Er.

As shown in FIG. 14, each auxiliary electrode Er (the counter electrode or the counter and reference electrodes) in the nucleic acid detection device of the fifth embodiment has a shape in which parts of the auxiliary electrode near the wall surfaces of the flow channel 110 are wide (long along the flow channel 110) and part of the auxiliary electrode near the center of the flow channel 110 (near the center of the two wall surfaces) is narrow (short along the flow channel 110). Thus, as is apparent from FIG. 14, in the nucleic acid detection device of this embodiment, under the condition that drops D dropped onto probe electrodes Ep and containing nucleic acid detection probes will not come into contact with the auxiliary electrodes Er, the probe electrodes Ep and the auxiliary electrodes Er can be arranged at shorter intervals than in the nucleic acid detection device that has the rectangular auxiliary electrodes Er shown in FIG. 13. This increases the density of the probe electrodes Ep. This contributes to downsizing, i.e., cost reduction, of a nucleic acid detection device 100.

Sixth Embodiment

The sixth embodiment is directed to another auxiliary electrodes Er that can replace the auxiliary electrodes Er in the nucleic acid detection device of the fifth embodiment. Namely, the arrangement of the nucleic acid detection device of the sixth embodiment is the same as that of the nucleic acid detection device of the fifth or first embodiment except for the difference in shape of the auxiliary electrodes Er.

Figure 15:
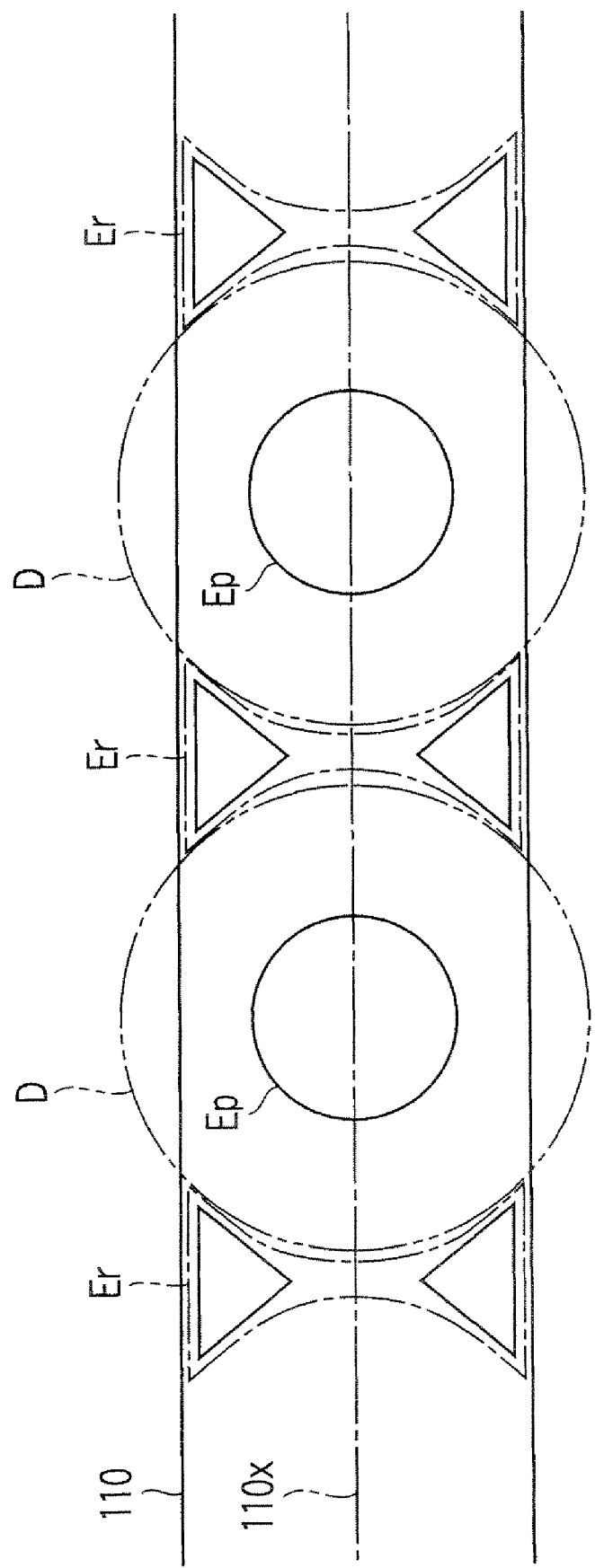
FIG. 15 shows probe electrodes and auxiliary electrodes in a nucleic acid detection device according to the sixth embodiment.

As shown in FIG. 15, each auxiliary electrode Er (the counter electrode or the counter and reference electrodes) in the nucleic acid detection device of this embodiment comprises two portions arranged so as to avoid a central line 110*x* of a flow channel 110. Each portion has the shape of, e.g., a triangle. The vertex of the triangle is located near the central line 110*x* of the flow channel 110, and its base is located near the wall surface of the flow channel 110.

Each portion constituting the auxiliary electrode Er is not limited to a triangle, and may have any shape in which part of the portion near the central line 110*x* of the flow channel 110 is narrow (short along the flow channel 110) and parts of the portion near the wall surfaces of the flow channel 110 are wide (long along the flow channel 110).

As is apparent from FIG. 15, in the nucleic acid detection device of this embodiment, under the condition that drops D dropped onto probe electrodes Ep and containing nucleic acid detection probes will not come into contact with the auxiliary electrodes Er, the probe electrodes Ep and the auxiliary electrodes Er can be arranged at shorter intervals than in the nucleic acid detection device that has the rectangular auxiliary electrodes Er shown in FIG. 13. Constituent portions of the auxiliary electrode Er do not exist near the central line 110*x* of the flow channel 110. Thus, the probe electrodes Ep and the auxiliary electrodes Er can be arranged at much shorter intervals than in the nucleic acid detection device of the fifth embodiment. This can be readily anticipated from FIG. 15. This increases the density of the probe electrodes Ep. This contributes to downsizing, i.e., cost reduction, of a nucleic acid detection device 100.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A nucleic acid detection device used to a target nucleic acid detection utilizing an electrochemical response of a nucleic acid recognition body, comprising:

a flow channel that allows a solution containing the nucleic acid recognition body to flow therethrough and includes a curved portion and a straight portion that is continued from and located downstream of the curved portion;

probe electrodes having immobilized nucleic acid probes and arranged at intervals along the straight portion so as to avoid an upstream end of the straight portion that is located within a distance L from the curved portion, the distance L being given by:

$$L = 0.065 \times Re \times D$$

$$Re = \rho u D / \mu$$

$$D = 4S/Lp$$

where $\rho$ is a concentration of the solution, u is a flow velocity of the solution, $\mu$ is a viscosity of the solution, S is a sectional area of the flow channel, and Lp is a wall peripheral perimeter of the flow channel; and at least one counter electrode provided in the flow channel and used to measure the electrochemical response of the nucleic acid recognition body.

2. A device according to claim 1, wherein the counter electrode is arranged somewhere within the curved portion and the upstream end.

3. A device according to claim 2, further comprising at least one reference electrode provided in the flow channel and used to measure the electrochemical response.

4. A device according to claim 3, wherein the reference electrode is arranged somewhere within the curved portion and the upstream end.

5. A device according to claim 1, wherein the counter electrode comprises counter electrodes, including the aforementioned at least one counter electrode, the flow channel comprises straight portions, including the aforementioned straight portion, and curved portions, including the aforementioned curved portion, and the probe electrodes are arranged so as to avoid the curved portions and upstream ends of the straight portions that are located within a distance L from downstream ends of the curved portions.

6. A device according to claim 5, wherein at least one of the counter electrodes is arranged somewhere within the curved portions and the upstream ends.

7. A device according to claim 5, wherein some of the probe electrodes and some of the counter electrodes alternately line up along the flow channel to form a row, and at least one counter electrode is located at at least one end of the row, the counter electrode being arranged somewhere within the curved portions and the upstream ends.

8. A device according to claim 3, wherein the counter electrode comprises counter electrodes, including the at least one counter electrode, the reference electrode comprises reference electrodes, including the aforementioned at least one reference electrode, the flow channel comprises straight portions, including the aforementioned straight portion, and curved portions, including the aforementioned curved portion, and the probe electrodes are arranged so as to avoid the curved portions and upstream ends of the straight portions that are located within a distance L from downstream ends of the curved portions.

9. A device according to claim 5, wherein at least one of the counter electrodes is arranged somewhere within the curved portions and the upstream ends, and at least one of the reference electrodes is arranged somewhere within the curved portions and the upstream ends.

10. A device according to claim 8, wherein some of the probe electrodes and some of the counter and reference electrodes alternately line up along the flow channel to form a row, and at least one of the counter and reference electrodes is located at least one end of the row, and one of the counter electrode and reference electrode is arranged somewhere within the curved portions and the upstream ends.

11. A device according to claim 5, wherein all the counter electrodes are arranged somewhere within the curved portions and the upstream ends.

12. A device according to claim 8, wherein all the counter and reference electrodes are arranged somewhere within the curved portions and the upstream ends.

13. A device according to claim 5, further comprising pads used for signal input/output and wirings connecting the pads to the probe and counter electrodes, wherein some of the counter electrodes are electrically, commonly connected to a first pad through a first wiring.

14. A device according to claim 13, wherein remaining ones of the counter electrodes are electrically, commonly connected to a second pad through a second wiring, and all the counter electrodes are arranged somewhere within the curved portions and the upstream ends.

15. A device according to claim 13, wherein some other ones of the counter electrodes are electrically, commonly connected to a second pad through a second wiring, and all the counter electrodes connected to the first and second pads are arranged somewhere within the curved portions and the upstream ends.

16. A device according to claim 8, further comprising pads used for signal input/output and wirings connecting the pads to the probe, counter, and reference electrodes, wherein some of the counter electrodes are electrically, commonly connected to a first pad through a first wiring, and the reference electrodes are electrically, commonly connected to one pad through one wiring.

17. A device according to claim 16, wherein remaining ones of the counter electrodes are electrically, commonly connected to a second pad through a second wiring, and all the counter electrodes are arranged somewhere within the curved portions and the upstream ends.

18. A device according to claim 8, further comprising pads used for signal input/output and wirings connecting the pads to the probe, counter, and reference electrodes, wherein the counter electrodes are electrically, commonly connected to one pad through one wiring, and the reference electrodes are electrically, commonly connected to another pad through another wiring.

19. A device according to claim 18, wherein the counter and reference electrodes are arranged somewhere within the curved portions and the upstream ends.

20. A device according to claim 1, wherein the counter electrode is located near a probe electrode and has a shape in which parts of the counter electrode near wall surfaces of the flow channel are wide and part of the counter electrode near a center of the flow channel is narrow.

21. A device according to claim 1, wherein the counter electrode is located near a probe electrode and includes portions arranged so as to avoid a central line of the flow channel.

22. A device according to claim 21, wherein each of the portions has a shape in which part of the counter electrode near the central line of the flow channel is narrow and part of the counter electrode near a wall surface of the flow channel is wide.

23. A device according to claim 1, wherein the counter electrode comprises counter electrodes, including the aforementioned at least one counter electrode, some of the counter electrodes alternate with some of the probe electrodes along the flow channel, and each of some of the counter electrodes has a shape in which parts of the counter electrode near wall surfaces of the flow channel are wide and part of the counter electrode near a center of the flow channel is narrow.

24. A device according to claim 1, wherein the counter electrode comprises counter electrodes, including the aforementioned at least one counter electrode, some of the counter electrodes alternate with some of the probe electrodes along the flow channel, and each of some of the counter electrodes includes portions arranged so as to avoid a central line of the flow channel.

25. A device according to claim 24, wherein each of the portions has a shape in which part of the counter electrode near the central line of the flow channel is narrow and part of the counter electrode near a wall surface of the flow channel is wide.

* * * * *